United States Patent [19]

Weitz et al.

[11] 4,100,361

[45] Jul. 11, 1978

[54] MANUFACTURE OF BUTENEDIOL DIACETATES

[75] Inventors: Hans-Martin Weitz, Bad Durkheim; Juergen Hartig, Ludwigshafen, both of Fed. Rep. of Germany

[73] Assignee: BASF Aktiengesellschaft, Ludwigshafen, Fed. Rep. of Germany

[21] Appl. No.: 727,799

[22] Filed: Sep. 29, 1976

[30] Foreign Application Priority Data

Oct. 11, 1975 [DE] Fed. Rep. of Germany ....... 2545698

[51] Int. Cl.$^2$ ............................................. C07C 67/05
[52] U.S. Cl. ................................................... 560/244
[58] Field of Search ................... 260/497 A; 560/244

[56] References Cited

U.S. PATENT DOCUMENTS

| | | | |
|---|---|---|---|
| 3,671,577 | 6/1972 | Ono et al. | 260/497 A |
| 3,755,423 | 8/1973 | Onoda et al. | 260/497 A |
| 3,922,300 | 11/1975 | Onoda et al. | 260/497 A |

FOREIGN PATENT DOCUMENTS

| | | | |
|---|---|---|---|
| 1,138,366 | 1/1969 | United Kingdom | 260/497 A |

*Primary Examiner*—Bernard Helfin
*Assistant Examiner*—Michael Shippen
*Attorney, Agent, or Firm*—Keil, Thompson & Shurtleff

[57] ABSTRACT

A process for the manufacture of butenediol diacetates, especially but-2-ene-1,4-diol diacetate and but-1-ene-3,4-diol diacetate, by reacting butadiene with oxygen and acetic acid in the gas phase or liquid phase over a solid catalyst which contains platinum and at least one element of main group 5 or 6, as well as nickel.

3 Claims, No Drawings

MANUFACTURE OF BUTENEDIOL DIACETATES

The present invention relates to a process for the manufacture of butenediol diacetates, especially but-2-ene-1,4-diol diacetate and but-1-ene-3,4-diol diacetate, by reacting butadiene with oxygen and acetic acid in the gas phase or liquid phase over a solid catalyst which contains platinum and at least one element of main group 5 or 6, as well as nickel.

German Laid-Open Application DOS 2,217,452 discloses the reaction of butadiene with oxygen and acetic acid in the liquid phase, in the presence of solid catalysts containing palladium, to give butenediol diacetates. The reaction can also be carried out in the gas phase over catalysts containing palladium and also containing alkali metal salts as promoters (German Laid-Open Application 2,200,124). A disadvantage of the liquid phase method is the low rate of reaction. Disadvantages of the gas phase reaction of the prior art are the formation of undesired by-products, e.g. 1-acetoxy-1,3-butadiene, and the need to carry out the reaction at low butadiene concentrations, so as not to reduce the activity of the catalyst.

We have found that butenediol diacetates, especially but-2-ene-1,4-diol diacetate, can be obtained in high yield and with a high space-time yield by reacting butadiene, oxygen and acetic acid over a solid catalyst, if the latter consists of platinum which contains at least one element of main group 5 or 6, selected from the group comprising phosphorus, arsenic, antimony, selenium or tellurium, and which additionally contains nickel.

The term "element", as used above, does not imply that the catalyst contains the particular material in atomic or metallic form. The catalyst is preferably a supported catalyst and can be obtained by the conventional method of manufacture of supported platinum catalysts.

For example, the catalyst can be manufactured by dispersing a carrier in a solution which has been obtained by dissolving a platinum compound and one or more phosphorus, arsenic, antimony, bismuth, tellurium and selenium compounds and a nickel compound in a suitable solvent, e.g. water; the solvent is then evaporated in order to deposit the above components on the carrier, and the mass is reduced in a stream of gas, comprising hydrogen or a reducing compound, or is reduced by means of conventional reducing agents, e.g. hydrazine, methanol or formalin. The catalyst can also be manufactured by adding a precipitant, (e.g. an alkaline reagent) to the mixture of carrier and solution, and then carrying out the reduction in accordance with the above process. Platinum and the remaining materials can be deposited simultaneously or successively on the carrier; in some cases, the carrier can be added in the form of a soluble compound and be precipitated conjointly with the catalytic materials.

Any method of reduction by which platinum, mixed with arsenic, antimony, bismuth, tellurium and/or selenium in addition to nickel is converted to the metallic state can be used. It is not certain in all cases whether the materials, other than platinum, after the treatment are present as the elements (i.e., in a zero valency, metallic state).

Carriers which may be used include active charcoal, silica gel, silicic acid, alumina, clay, bauxite, magnesia, kieselguhr, pumice and the like. The carriers can be activated by conventional methods, e.g. by treatment with acids.

The platinum compound used to manufacture the catalyst is not a particularly decisive factor, though, for cost reasons, it is advantageous to use a halogen-containing platinum compound, e.g. platinum-II chloride or platinum-IV chloride, a platinum salt of an organic acid, such as platinum acetate, platinum nitrate, platinum oxide and the like. Of course it is, however, also possible to use other platinum compounds, e.g. hexachloroplatinic acid, sodium platinum sulfate and the like.

As a rule, the platinum concentration on the carrier is from 0.1 to 20% by weight, though higher and lower concentrations can be used.

There are also no particular limitations as regards the compounds used as the further components for the manufacture of the catalyst; halides, nitrates, sulfates, oxides and other compounds of this type may be employed. Suitable phosphorus compounds are, inter alia, orthophosphoric acid, metaphosphoric acid, alkali metal phosphates and alkaline earth metal phosphates.

Though a wide range of amounts of phosphorus, arsenic, antimony, bismuth, tellurium and selenium compounds deposited on the carriers results in an active catalyst, amounts of from 0.05 to 30% by weight are generally advantageous; in the case of nickel, from 0.01 to 1.0% by weight as a rule suffices.

Particularly preferred and exceptionally suitable catalysts are platinum catalysts of the above type which contain active charcoal as the support and from about 0.1 to 5% of tellurium or antimony in addition to from 0.1 to 10% of platinum (based on the total weight of catalyst).

Higher concentrations of platinum than those stated can also be used, but produce no economic advantage, since we have not observed an increase in space-time yield or in olefin conversion proportional to the increase in the metal concentration.

The reaction to be catalyzed can be carried out in the gas phase or liquid phase, in accordance with any conventional process, continuously or batchwise, for example using a fixed bed, fluidized bed, three-phase flow bed and the like, the chosen state of aggregation of the reaction medium being the deciding factor in each case.

If the reaction is carried out in the liquid phase, the process can be conducted safely, and with a high space-time yield, by reacting acetic acid with dissolved butadiene and dissolved oxygen over a solid catalyst, for example in a trickle tower. It is possible and particularly advantageous to avoid the presence of a gas phase. The space-time yield is here defined as the yield of diacetate in g, per liter of catalyst per hour. A trickle tower is an arrangement in which the catalytically active packing is placed in a vertical (L/D ratio > 1) gas-filled tubular reactor, and liquid is fed in at the top. If the process is carried out in a tubular reactor completely filled with liquid, it is immaterial whether the products are fed into the reactor from the top or the bottom.

A further possible method of carrying out the process is to react butadiene and acetic acid in the presence of a suspended catalyst in a stirred apparatus or stirred flask, under atmospheric or superatmospheric pressure.

The reaction temperature is generally from 60° to 120° C, preferably from 70° to 110° C. Whilst in principle temperatures below 60° C can be used, they result in a rapid drop in the space-time yield. Equally, temperatures above 120° C can be used, but result in increased formation of by-products.

The reaction pressure can vary from about 1 to 1,000 bars and is in general from atmospheric pressure to about 325 atmospheres, depending on the process details.

The reaction temperature in the gas phase is in general from 100° to 180° C, preferably from 120° to 150° C. The reaction pressure is determined by the process details and is in general from atmospheric pressure to about 100 atmospheres.

The butenediol diesters which can be manufactured by the process of the invention are valuable intermediates, for example for the manufacture of butenediol and butanediol. Butene-3,4-diol diacetate (vinyl-glycol acetate), which is formed in minor amounts, is an intermediate for the manufacture of vitamins and other biologically active compounds.

EXAMPLE 1

25 mmoles of platinum chloride (8.43 g), 25 mmoles of tellurium oxide (3.99 g) and 0.1 mmole of nickel chloride. $6H_2O$ (0.024 g) are dissolved in 200 ml of 6 N hydrochloric acid; 50 g of active charcoal (0.1–0.4 mm $\phi$) previously extracted by boiling with 15% strength nitric acid, are added and the mixture is slowly evaporated to dryness on a waterbath. After further drying, by passing a stream of nitrogen at 150° C through the catalyst in a tube for 2 hours, the material is reduced by now saturating the stream of nitrogen with methanol at room temperature and using it to treat the catalyst at a rate of 5 l/minute, first for 4 hours at 200° C and then for 2 hours at 400° C.

25 g of the catalyst thus obtained and 540 g of acetic acid are filled into a stirred flask. A mixture of 3 l (S.T.P.)/hour of butadiene and 3 l (S.T.P.)/hour of oxygen is passed in at 85° C. After 4 hours the reaction is discontinued, the catalyst is separated off and the solution is concentrated and distilled. 46.6 g of diacetates are obtained, the butadiene conversion being 50.5%. The distillate is made up of 81.3% of but-2-ene-1,4-diol diacetate and 18.6% of but-1-ene-3,4-diol diacetate. The space-time yield (STY) is 186 g per liter per hour (g/l.h).

COMPARATIVE EXPERIMENT 1

25 mmoles of platinum chloride (8.43 g) and 25 mmoles of tellurium oxide (3.99 g) are dissolved in 200 ml of 6 N hydrochloric acid; 50 g of active charcoal (0.1–0.4 mm $\phi$) previously extracted by boiling with 15% strength nitric acid, are added and the mixture is slowly evaporated to dryness on a waterbath. After further drying, by passing a stream of nitrogen gas at 150° C through the catalyst in a tube for 2 hours, the material is reduced by passing in a stream of nitrogen gas, which is saturated with methanol at room temperature, at a rate of 5 l/minute for 4 hours at 200° C and then for 2 hours at 400° C. 25 g of the catalyst thus produced and 540 g of acetic acid are introduced into a stirred flask.

A mixture of 3 l (S.T.P.)/hour of butadiene and 3 l (S.T.P.)/hour of oxygen is passed in under the same conditions as in Example 1, at 85° C. After 4 hours the reaction is discontinued, the catalyst is separated off and the solution is concentrated and distilled. 36.8 g of diacetates are obtained, the butadiene conversion being 33%. The distillate comprises 81.2% of but-2-ene-1,4-diol diacetate and 18.8% of but-1-ene-3,4-diol diacetate (STY = 147 g/l.h).

EXAMPLE 2

91.1 mmoles (30.717 g) of platinum chloride, 25.1 mmoles (4.004 g) of tellurium dioxide and 0.82 mmoles (0.195 g) of nickel chloride ($NiCl_2.6H_2O$) are dissolved in 3,000 ml of 6 N hydrochloric acid; 300 g of active charcoal (4 mm $\phi$) are added and the mixture is slowly evaporated to dryness on a waterbath. After further drying, by passing a stream of nitrogen gas at 150° C through the catalyst in a tube for 2 hours, the material is reduced by passing in a stream of nitrogen gas, which is saturated with methanol at room temperature, at a rate of 5 l/minute for 10 hours at 200° C and then for 3 hours at 400° C.

150 g of the catalyst thus produced are introduced into a jacketed tube ($\phi$ 32 mm; L = 50 cm). At 130° C, 10.5 l (S.T.P.) of butadiene, 10.5 l (S.T.P.) of oxygen and 250 ml of acetic acid are introduced per hour. The acetic acid is heated to 130° C in a vaporizer, and is introduced as vapor.

Samples are taken hourly and worked up by distillation. According to analysis, the distillate contains more than 99% of butenediol diacetates. The space-time yields after 4, 11 and 32 hours are respectively 42, 40 and 35 g per kg of catalyst per hour.

EXAMPLE 3

72 g of platinum tetrachloride, 8.2 g of tellurium dioxide and 0.35 g of nickel chloride ($NiCl_2.6H_2O$) are dissolved in 4,000 ml of 6 N hydrochloric acid; 500 g of active charcoal (0.2–0.4 mm $\phi$) previously extracted by boiling with 15% strength nitric acid, are added and the mixture is slowly evaporated to dryness on a waterbath. After further drying, by passing a stream of nitrogen gas at 150° C through the catalyst in a tube for 20 hours, the material is reduced by passing in a stream of nitrogen gas, which is saturated with methanol at room temperature, at a rate of 50 l/minute for 10 hours at 200° C and then for 10 hours at 400° C.

0.5 g of the catalyst thus produced is filled into a reaction tube (length 4,000 mm, $\phi$ 20 mm). Glass rings are introduced above the catalyst. Per hour, 0.75 l of liquid butadiene, 6 l of acetic acid and 20 l (S.T.P.) of oxygen are introduced, at 29 bars and 95° C, into a mixing device (a 4,000 × 6 mm tube filled with metal helices). An inspection window is provided above the mixing device for the purpose of checking that the oxygen has dissolved completely.

The solution thus obtained is passed into the top of the reactor. The reaction product which issues is passed into a separator, from where it is continuously withdrawn from the installation. Over a period of 250 hours, the space-time yield averages 115 g/l.h. The diacetate product comprises 18% of but-1-ene-3,4-diol diacetate and 81.5% of but-2-ene-1,4-diol diacetate.

We claim:

1. A process for the manufacture of butenediol diacetates, which comprises: reacting butadiene with oxygen and acetic acid in the liquid phase in contact with an effective amount of a supported catalyst at a pressure from about 1 to 1,000 bars and at a temperature of about 60° to 120° C in which the carrier is active charcoal, wherein the catalyst used contains from about 0.1 to 10% by weight, based on the weight of the catalyst, of platinum, from about 0.1 to 5% by weight, based on the weight of the catalyst, of at least one element selected from the group consisting of tellurium and antimony, and additionally contains from about 0.01 to 1.0% by weight, based on the weight of catalyst, of nickel.

2. A process as set forth in claim 1, wherein the pressure is from about atmospheric to 325 atmospheres.

3. A process as set forth in claim 2, wherein the temperature is from about 70° to 110° C.

* * * * *